(12) United States Patent
Albrecht et al.

(10) Patent No.: US 7,271,148 B2
(45) Date of Patent: Sep. 18, 2007

(54) INHIBITION OF CELLULAR PROTEASES

(75) Inventors: Thomas B. Albrecht, Galveston, TX (US); Zhenping Chen, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 09/748,642

(22) Filed: Dec. 22, 2000

(65) Prior Publication Data

US 2002/0049175 A1 Apr. 25, 2002

Related U.S. Application Data

(60) Provisional application No. 60/172,004, filed on Dec. 23, 1999.

(51) Int. Cl.
| | |
|---|---|
| *A61K 38/00* | (2006.01) |
| *C07K 5/00* | (2006.01) |
| *C07K 7/00* | (2006.01) |
| *C12N 5/00* | (2006.01) |
| *A61K 39/25* | (2006.01) |
| *A61K 39/245* | (2006.01) |

(52) U.S. Cl. .................. 514/12; 530/324; 530/325; 530/326; 514/13; 435/325; 424/230.1

(58) Field of Classification Search .......... 514/2, 514/19, 475, 44, 12, 13
See application file for complete search history.

(56) References Cited

U.S. PATENT DOCUMENTS

| | | | |
|---|---|---|---|
| 5,478,727 A | 12/1995 | Roizman et al. | |
| 5,607,831 A | 3/1997 | Henkart et al. | |
| 5,684,147 A | 11/1997 | Agrawal et al. | |
| 5,776,718 A | 7/1998 | Palmer et al. | |
| 5,776,933 A | 7/1998 | Gordon et al. | |
| 5,886,036 A | 3/1999 | Kempf et al. | |
| 5,981,259 A | 11/1999 | Franzusoff | |
| 6,015,787 A * | 1/2000 | Potter et al. | 514/12 |
| 6,294,518 B1 * | 9/2001 | Potter et al. | |
| 6,410,704 B1 * | 6/2002 | Roizman et al. | |

FOREIGN PATENT DOCUMENTS

EP 0514830 A2 11/1992

OTHER PUBLICATIONS deJong et al. Summary of the II International Symposium on Cytomegalovirus (mini review). 1998 Antiviral Research, vol. 39: pp. 141-162.*
Chen et al. Proceedings of the American Association for Cancer Research Annual Meeting, (Mar. 1999) vol. 40, pp. 447-448. print. Meeting Info.: 90th Annual Meeting of the American Association for Cancer Research. Philadelphia, Pennsylvania, USA. Apr. 10-14, 1999.*
Kleina et al., Antiviral effects of a thiol protease inhibitor on foot-and-mouth disease virus, Dec. 1992, Journal of Virology, vol. 66, pp. 7168-7175.*
Kim et al., Coronavirus protein processing and RNA synthesis is inhibited by the cystein proteinase inhibitor E64d, 1995, Virology, vol. 208, pp. 1-8.*
Debaisi et al., "Reovirus-Induced Apoptosis Is Preceded by Increased Cellular Calpain Activity and Is Blocked by Calpain Inhibitors", Journal of Virology 73(1):695-701 (Jan. 1999).
Huang et al., "Ester and Amide Derivatives of E64c as Inhibitors of Platelet Calpains", J Med Chem 35:2048-2054 (1992).
McGowan et al., "Inhibition of Calpain in Intact Platelets by the Thiol Protease Inhibitor E-64d", Biochem Biophys Res Com 158(2):432-435 (1989).
Rossi et al., "Activation of the Heat Shock Factor 1 by Serine Protease Inhibitors", J Biol Chem 273(26):16446-16452 (1998).
Chen et al., J. Virology, 75(8):3613-3625 (2001).
Carafoli et al., Biochemical & Biophysical Research Communications, 247:193-203(1998).
Sicar et al., Antiviral Research 30:147-53(1996).
Everett et al., The EMBO J., 17(24):7161-769(1998).
Bresnahan et al., Virology, 224:150-160(1996).
Kido et al., Biol. Chem., 378:255-63(1997).
Kido et al., Advances in Enzyme Regualtion, 36:325-347(1996).
Kido et al., Biopolymers, 51:79-86(1996).

* cited by examiner

*Primary Examiner*—J. Douglas Schultz
*Assistant Examiner*—Dana Shin
(74) *Attorney, Agent, or Firm*—Rogalskyj & Weyand, LLP

(57) ABSTRACT

The invention provides a method of decreasing viral replication in cells, the method comprising decreasing levels of functional cellular protease in the cells. The invention further provides a method of treating or preventing a viral infection in a subject, the method comprising administering to the subject an amount of a compound effective to decrease levels of functional cellular protease in the cells of the subject.

4 Claims, 10 Drawing Sheets

WESTERN BLOT

WESTERN BLOT

CALPAIN     −   +   +

E64d     −   −   +

$p21^{cip1}$

COOMASSIE BRILLIANT BLUE STAIN

M     $p21^{cip1}$     CASEIN m-CALPAIN     −   +   −   −   +   −

μ-CALPAIN     −   −   +   −   −   +

US 7,271,148 B2

INHIBITION OF CELLULAR PROTEASES

This application claims priority of U.S. Provisional Patent Application 60/172,004, filed Dec. 23, 1999.

This invention was made with support from the United States Government under Grant No. RO1DE11389-01. The U.S. Government may have certain rights in this invention.

FIELD OF THE INVENTION

The subject invention is directed generally to a method for treating or preventing a viral infection, by decreasing viral replication in cells, and more particularly to decreasing levels of functional cellular protease in order to decrease viral replication.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Human herpesviruses are major causes of adverse health effects. Human cytomegalovirus (HCMV), for example, is a major cause of birth defects, transplantation failure, and devastating disease in immunocompromised individuals. Herpesviruses and other DNA viruses such as papillomaviruses are particularly difficult problems for humans, because they form life-long persistent infections. An additional discussion of viral infections, in particular human cytomegalovirus infections, can be found in U.S. Pat. Nos. 4,663,317, 4,782,065, 4,800,081, and 4,849,412, the contents of each of which are incorporated herein.

Although some drugs have been developed that are efficacious in treating these virus infections, drug-related toxicity and development of drug-resistant virus strains have compromised their impact on treatment of these virus infections. These findings indicate that new therapeutic approaches are needed for these infections.

Human cytomegalovirus infection is widespread among human populations, primarily as a subclinical persistent infection, although HCMV infection is a major cause of morbidity and mortality in several well-studied risk groups. Those most severely affected by HCMV infection include congenitally infected infants and individuals whose immune systems are compromised, particularly with HIV infection or immunosuppressive therapy for tissue transplantation (for reviews, see 8, 27, 59, 63). The clinical management of these infections is still problematic, even though several agents have been identified with potent antiviral activity for HCMV infection both in vitro and in vivo. Unfortunately, the toxicity associated with the long-term use of these drugs makes clinical management difficult, and drug resistant strains have emerged (for a review, see 54). Thus, there continues to be great interest in improving the understanding of the replication of HCMV with a view towards developing more effective approaches to control these infections.

HCMV replication seems to be closely associated with extensive modifications of cellular metabolism (reviewed in 4, 5), leading to a number of physiologic changes and activation of a large number of cellular genes (76). Initially, HCMV infection induces a series of cellular responses that in many ways resembles the immediate early events observed following activation of serum-arrested cells by serum growth factors (4). These events include: hydrolysis of phosphatidylinositol 4,5-bisphosphate ($PIP_2$), yielding increased cellular levels of sn-1,2-diacylglycerol (DG) and inositol 1,4,5-trisphosphate ($IP_3$) (69); increased release of arachidonic acid and its metabolites (1,2); changes in $Ca^{2+}$ homeostasis, including $Ca^{2+}$ influx, release of $Ca^{2+}$ stores, and an increase in intracellular free $Ca^{2+}$ (51); transcriptional activation of cellular oncogenes c-fos, c-jun, and c-myc (11,12,13); and increased activity of the DNA-binding proteins NFκB, AP-1, and CREB (14). The signaling cascade induced by HCMV infection induces a robust mitogenic response. This is evidenced by the ability of HCMV to stimulate density-arrested cells, which are resistant to stimulation by serum growth factors, to enter the cell cycle (18). Recent results indicate that productive HCMV infection stimulates cell cycle progression in either serum- or density-arrested cells through late G1 phase to a point at or near the G1/S boundary (18,28,46). Closely associated with this limited traverse of the cell cycle is an increase in cyclin E/cyclin-dependent kinase 2 (Cdk2) activity (18) and hyperphosphorylation of pRb, releasing E2F (41). Activation of E2F, together with MYC, leads to an increase in the cellular levels of a large number of genes involved in nucleotide biosynthesis, priming the infected cell for DNA synthesis (e.g., 5,7).

Three HCMV-induced events appear to be necessary for activation of E kinase activity: 1) transcriptional activation of cyclin E (16), 2) translocation of Cdk2 from the cytoplasm to the nucleus (19), and 3) a substantial decrease in the nuclear levels of the cyclin kinase inhibitors (CKIs) $p21^{cip1/waf1}$ (hereafter $p21^{cip1}$) and $p27^{kip1}$ (18). Activation of E kinase appears to be critical for efficient HCMV replication, since drugs that interfere with the activity of Cdk2 substantially reduce infectious yields (17). The precise mechanisms through which these virus-induced cellular modifications are achieved are poorly understood at this time.

$p21^{cip1}$ is a potent inhibitor of Cdks (e.g., 37,38,71) and is a critical p53 downstream effector in the growth suppressive pathway (31). $p21^{cip1}$ binds cyclin/Cdk complexes, thereby inhibiting the activity of Cdks, such as Cdk2, Cdk3, Cdk4, and Cdk6, and consequently inhibiting cell cycle progression. In addition, $p21^{cip1}$ interacts with proliferating cell nuclear antigen (PCNA) (34) and gadd45 (42), affecting their function, e.g., interfering with DNA replication and repair (22,34,45,53,55,70,73). $p21^{cip1}$ may also be involved in p53-mediated apoptosis (36) and in the control of cell senescence (50). Despite significant advances in the understanding of how $p21^{cip1}$ exerts its biological effects and is transcriptionally regulated, there is only limited information available on how the stability of the $p21^{cip1}$ protein is regulated under the physiologic conditions associated with disease and other forms of stress. Non-lysosomal cytoplasmic protease systems have been identified as important regulators of cell cycle progression (24,26,33,52,61,62). Two prominent cytoplasmic protease pathways have been identified—the ubiquitin-proteasome and calpain pathways. Many cell cycle regulatory proteins that are degraded at specific points in the cell cycle, e.g., cyclins A, B, and E, are substrates of the ubiquitin/proteasome pathway. It has also been reported that $p21^{cip1}$ is subject to proteolysis by ubiquitin-mediated proteasome degradation (10,33,35,72).

SUMMARY OF THE INVENTION

The subject invention provides a method of decreasing viral replication in cells, the method comprising decreasing levels of functional cellular protease (CP) in the cells. The invention further provides a method of treating or preventing a viral infection in a subject, the method comprising administering to the subject an amount of a compound effective to decrease levels of functional cellular protease in cells of the subject.

Human cytomegalovirus (HCMV) stimulates arrested cells to enter the cell cycle by activating cyclin-dependent kinases (Cdks). HCMV causes a substantial increase in the abundance of cyclin E, translocation of Cdk2 from cytoplasm to the nucleus, depletes $p21^{cip1/Waf1}$ ($p21^{cip1}$) and $p27^{kip1}$ and increases the activity of cyclin E/Cdk2. In accordance with the subject invention, the mechanism responsible for the decrease in $p21^{cip1}$ abundance were investigated by measuring the effect of HCMV infection on $p21^{cip1}$ RNA and protein levels in permissive human lung (LU) fibroblasts. Northern blot analysis revealed that $p21^{cip1}$ RNA levels increased briefly after 3 hr of HCMV infection, fell off dramatically thereafter, and then increased modestly. Western blot analysis demonstrated that $p21^{cip1}$ protein abundance did not closely follow the observed changes in RNA levels. After a transient increase at 3 hr post-infection (PI), $p21^{cip1}$ abundance declined sharply over the next 24 hr and remained at a low level through 96 hr PI. The observed disparity between $p21^{cip1}$ RNA and protein levels suggested that $p21^{cip1}$ might be degraded in HCMV-infected cells. Treatment with MG132, an inhibitor of proteasome-mediated proteolysis, provided substantial protection of $p21^{cip1}$ in mock-infected cells, but MG132 was much less effective in protecting $p21^{cip1}$ in HCMV-infected cells. The addition of E64d and Z-Leu-Leu-H, inhibitors of calpain activity, to HCMV-infected cells substantially increased the amounts of $p21^{cip1}$ in a concentration-dependent manner. To verify that $p21^{cip1}$ was a substrate for calpain, purified recombinant $p21^{cip1}$ was incubated with either m-calpain or μ-calpain, resulting in rapid proteolysis of $p21^{cip1}$. E64d inhibited the proteolysis of $p21^{cip1}$ catalyzed by either m- or μ-calpain. Direct measurement of calpain activity in HCMV-infected LU cells indicated that HCMV infection induced a substantial and sustained increase in calpain activity, although there was no change in the abundance of either m- or μ-calpain, or the endogenous calpain inhibitor calpastatin. The observed increase of calpain activity is consistent with the increase in $[Ca^{2+}]_i$ and phospholipid degradation in HCMV-infected LU cells reported previously. Taken together, these results teach that the observed increase in calpain activity following HCMV infection contributes significantly to the reduction of $p21^{cip1}$ abundance and resultant cell cycle progression.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

Figure 1:
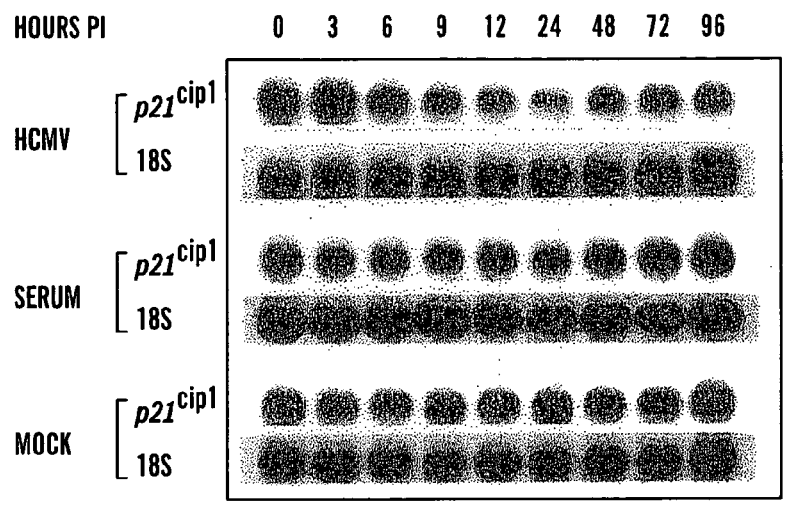
FIG. 1 is a Northern blot showing the effect of HCMV infection, serum growth factors, or mock infection on RNA levels for $p21^{cip1}$ in density-arrested LU cells.

The subject invention is based on the discovery that decreasing levels of functional cellular protease (CP) in a cell (such as by decreasing cellular protease (CP) gene expression or by decreasing activity of CP) can decrease viral infection in cells.

Decreasing "levels" of functional CP refers to decreasing expression of the CP gene, or decreasing activity of the CP protein.

The invention thus provides a method of decreasing viral replication in cells, the method comprising decreasing levels of CP in the cells of the subject. This method can be used, for example, to prevent or treat viral infections of cell cultures.

Levels of CP in the cells can be decreased by various methods, at the gene and protein levels. In one embodiment, the levels are decreased by decreasing CP gene expression of the CP protein in the cells. This can be accomplished by exposing the cells to a compound which decreases CP gene expression of the CP protein. The compound could be, for example, an antisense oligonucleotide targeted to the CP gene.

In a similar embodiment, the compound which decreases CP gene expression of the CP protein could be a ribozyme, which is a special category of antisense RNA molecule having a recognition sequence complementary to the mRNA encoding the CP. A ribozyme not only complexes with a target sequence via complementary antisense sequences, but also catalyzes the hydrolysis, or cleavage, of the template mRNA molecule. The expression of the CP protein is therefore prevented.

Other methods for decreasing CP gene expression could also involve site-directed mutagenesis of the CP gene to prevent expression of the CP, or various gene therapy techniques. It may be desirable to alter the expression of the CP gene in such a way that expression of the CP is inducible, allowing the controlled increase or decrease in expression of CP.

Levels, in particular activity, of CP in the cell can also be decreased by exposing the cells to an inhibitor of the CP. Currently known inhibitors of CPs include, for example, E64d, Z-Leu-Leu-H, and related compounds. Other inhibitors of the CP could also readily be identified by various screening methods used in the art (see more detailed discussion below). In addition to chemical inhibitors, peptide inhibitors could also be identified with currently known screening methods (for example, using phage display libraries and other peptide screening methods).

Since the method of the subject invention is a method of decreasing viral replication in cells, the cells of interest can be of human or animal origin, in vitro or in vivo.

The invention further provides a method of treating or preventing a viral infection in a subject, the method comprising administering to the subject an amount of a compound effective to decrease levels of CP in the cells of the subject. As above, the compound may decrease levels of CP by decreasing CP gene expression of the CP, or by inhibiting the CP.

The method is useful in a viral infection. Examples of viruses causing such infections include DNA viruses, such as human cytomegalovirus, herpes simplex virus, and varicella zoster virus.

In one embodiment, the invention employs oligonucleotides targeted to nucleic acids encoding functional cellular protease (CP). The relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. In the subject invention, this may be, for example, the cellular gene (or mRNA made from the gene) for CP; i.e., the target is a nucleic acid encoding CP, the CP gene, or mRNA expressed from the CP gene. The targeting process also includes determination of a site or sites within the nucleic acid sequence for the oligonucleotide interaction to occur such that the desired effect, modulation of gene expression, will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of CP gene expression is presently the preferred form of modulation. This modulation can be measured in ways which are routine in the art, for example by Northern blot assay of mRNA expression or Western blot assay of protein expression. Effects on viral replication can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In various embodiments of this invention, oligonucleotides are provided which are targeted to mRNA encoding CP. In accordance with this invention, persons of ordinary skill in the art will understand that mRNA includes not only the coding region which carries the information to encode a gene product using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. The functions of mRNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with CP gene expression.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The compounds and/or inhibitors used in the methods of the subject invention encompass any pharmaceutically acceptable salts, esters, or salts of such esters, or any other compound/inhibitor which, upon administration to an animal including a human, is capable of providing (directly or indirectly) the biologically active metabolite or residue thereof. Accordingly, for example, the disclosure is also drawn to prodrugs and pharmaceutically acceptable salts of the compounds and/or inhibitors used in the subject invention, pharmaceutically acceptable salts of such prodrugs, and other bioequivalents.

In regard to prodrugs, the compounds and/or inhibitors for use in the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions.

In regard to pharmaceutically acceptable salts, the term pharmaceutically acceptable salts refers to physiologically and pharmaceutically acceptable salts of the compounds and/or inhibitors used in the subject invention: i.e., salts that retain the desired biological activity of the parent compound and do not impart undesired toxicological effects thereto.

The oligonucleotides used in the method of the subject invention preferably are from about 8 to about 50 nucleotides in length. In the context of this invention it is understood that this encompasses non-naturally occurring oligomers, preferably having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the skill of the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In the context of this invention, to "expose" cells (including the cells of tissues) to a compound and/or inhibitor means to add the compound and/or inhibitor, usually in a liquid carrier, to a cell suspension or tissue sample, either in vitro or ex vivo, or to administer the compounds and/or inhibitor to cells or tissues within an animal (including a human) subject.

For therapeutics, methods of decreasing viral replication in cells and methods of preventing and treating viral infection are provided. The formulation of therapeutic compositions and their subsequent administration is believed to be within the skill in the art. In general, for therapeutics, a patient suspected of needing such therapy is given a compound and/or inhibitor in accordance with the invention, commonly in a pharmaceutically acceptable carrier, in amounts and for periods which will vary depending upon the nature of the particular disease, its severity and the patient's overall condition. The pharmaceutical compositions may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is LIPOFECTIN™ (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual compounds and/or inhibitors, and can generally be calculated based on $IC_{50}$'s or $EC_{50}$'s or viral infectivity levels in vitro and in vivo animal studies. For example, given the molecular weight of a compound (derived from oligonucleotide sequence and/or chemical structure) and an effective dose such as an $IC_{50}$, for example (derived experimentally), a dose in mg/kg is routinely calculated.

The nucleic acid and amino acid sequences of various cellular protease genes are known and readily available from GenBank and described in the literature.

Given these sequences, one can design appropriate antisense molecules for use in the subject invention. Furthermore, by expressing the functional CP in a host cell, one can screen for suitable compounds and/or inhibitors for use in the subject invention. The function of the encoded cellular protease can be assayed according to methods known in the art. For example, for the CP calpain one can assay by analysis of levels of p21. As used herein, "functional" expression refers to the synthesis and any necessary post-translational processing of a CP molecule in a cell so that the CP is active.

More particularly, having known nucleic acid molecules encoding the CP, a method for screening a chemical agent (compound or inhibitor) for the ability of the chemical agent to modify CP function begins by introducing the nucleic acid molecule encoding the CP into a host cell, and expressing the CP encoded by the molecule in the host cell. The expression results in the functional expression of a CP in the host cell. The cell is then exposed to a chemical agent and evaluated to determine if the chemical agent modifies the function of the CP. From this evaluation, chemical agents effective in altering the function of the CP can be found and utilized in the methods of the subject invention.

Drugs, such as peptide drugs, which inhibit the CP can be made using various methods known in the art. Initially, a monoclonal antibody can be prepared which specifically hybridizes to the CP, thereby interfering with activity.

The monoclonal antibodies can be produced by hybridomas. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell, A. M., "Monoclonal Antibody Technology: Laboratory Techniques in Biochemistry and Molecular Biology", Elsevier Science Publishers, Amsterdam, The Netherlands (1984); St. Groth, et al., J Immunol Methods 35:1-21 (1980)). Any animal (mouse, rabbit, etc.) which is known to produce antibodies can be immunized with the CP (or an antigenic fragment thereof). Methods for immunization are well known in the art. Such methods include subcutaneous or intraperitoneal injection of the CP. One skilled in the art will recognize that the amount of the CP used for immunization will vary based on the animal which is immunized, the antigenicity of the CP, and the site of injection.

The CP which is used as an immunogen may be modified or administered in an adjuvant in order to increase the CP's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz, et al., Exp Cell Res 175:109-124 (1988)).

Hybridomas secreting the desired antibodies are cloned and the class and subclass are determined using procedures known in the art (Campbell, A.M., "Monoclonal Antibody Technology: Laboratory Techniques in Biochemistry and Molecular Biology", Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

Once a monoclonal antibody which specifically hybridizes to the CP is identified, the monoclonal (which is itself a compound or inhibitor which can be used in the subject invention) can be used to identify peptides capable of mimicking the inhibitory activity of the monoclonal antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., Gene 73:305-318 (1988)). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley, S. F. & Smith, G. P., Gene 73:305-318 (1988); Cwirla, S. E., et al., Proc Natl Acad Sci USA 87:6378-6382 (1990); Scott, J. K. & Smith, G. P., Science 249:386-390 (1990); Christian, R. B., et al., J Mol Biol 227:711-718 (1992); Smith, G. P. & Scott, J. K., Methods in Enzymology 217:228-257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., Gene 73:305-318 (1988); Scott, J. K., Trends in Biochem Sci 17:241-245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally-occurring molecule, i.e. a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes CP can be identified. The sequences of these mimotopes represent short peptides which can then be used in various ways, for example as peptide drugs that bind to CP and decrease the activity of CP. Once the sequence of the mimotope is determined, the peptide drugs can be chemically synthesized.

The peptides for use in the subject invention can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptide depends, in part, on the desired characteristics of the peptide. For example, the incorporation of one or more (D)-amino acids can confer increased stability on a peptide and can allow a peptide to remain active in the body for an extended period of time. The incorporation of one or more (D)-amino acids can also increase or decrease the pharmacological activity of a peptide.

The peptide may also be cyclized, since cyclization may provide the peptide with superior properties over their linear counterparts.

Modifications to the peptide backbone and peptide bonds thereof are encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC 46:257 (1981) and Raucher et al., Tetrahedron Lett 21:14061 (1980). An amino acid mimic is, therefore, an organic molecule that retains the similar amino acid pharmacophore groups as are present in the corresponding amino acid and which exhibits substantially the same spatial arrangement between functional groups.

The substitution of amino acids by non-naturally occurring amino acids and amino acid mimics as described above can enhance the overall activity or properties of an individual peptide thereof based on the modifications to the backbone or side chain functionalities. For example, these types of alterations can enhance the peptide's stability to enzymatic breakdown and increase biological activity. Modifications to the peptide backbone similarly can add stability and enhance activity.

One skilled in the art, using the identified sequences can easily synthesize the peptides for use in the invention. Standard procedures for preparing synthetic peptides are well known in the art. The novel peptides can be synthesized using: the solid phase peptide synthesis (SPPS) method of Merrifield, J Am Chem Soc 85:2149 (1964) or modifications of SPPS; or, the peptides can be synthesized using standard solution methods well known in the art (see, for example, Bodanzsky, "Principles of Peptide Synthesis", 2d Ed., Springer-Verlag (1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc Natl Acad Sci USA 82:5131 (1985).

Materials and Methods

Cell culture and growth arrest. LU cells (3) were propagated in Eagle's minimum essential medium containing 10% fetal bovine serum and penicillin (100 units/ml)/streptomycin (100 μg/ml) in a 5% $CO_2$ in air atmosphere. The cells were density-arrested as described previously in detail (18).

Virus stocks and productive infection. The AD169 strain of HCMV was propagated in LU cells as previously described in detail (6). The infectivity of virus stocks was determined by plaque assay (3). Virus stocks typically had infectivities between $8.0 \times 10^6$ and $4.0 \times 10^7$ plaque-forming units (PFU)/milliliter. LU cells were infected with HCMV as described in detail by Bresnahan et al. (18). Virus stocks and cell cultures were routinely examined for mycoplasma.

RNA isolation. RNA was extracted using Tri Reagent (Molecular Research Center, Inc., Cincinnati, Ohio), which contains phenol and guanidine thiocyanate (23). Cells were lysed in Tri Reagent and the phases were separated by sedimentation. The RNA was precipitated from the aqueous phase with isopropanol and collected by sedimentation. The RNA pellets were washed with 70% ethanol and then dissolved in diethylpyrocarbonate (DEPC)-treated water.

Preparation of probes. A DNA probe was prepared from the plasmid pC-waf1-S (31), which harbors a $p21^{cip1}$ insert. A probe derived from the plasmid p5B (15), which contains the cDNA for 18S rRNA, was used to monitor gel loading. The plasmids were introduced into competent DH5α E. coli cells and amplified. The amplified plasmids were isolated and the probes recovered by restriction enzyme digestion. The $p21^{cip1}$ probe was obtained from the plasmid DNA as a NotI fragment, while the 18S probe was a BamHI-EcoRI fragment of the plasmid DNA. The probes were labeled using the multiprimer labeling kit (Amersham Pharmacia Biotech, Piscataway, N.J.).

Electrophoresis and Northern hybridization. Northern hybridization was performed as described previously (16). Total cellular RNA (20 μg/lane) was evaluated under denaturing conditions in formaldehyde gels. The denaturing agarose gels contained 1% agarose, 20 mM 3-[N-morpholino]propanesulfonic acid (MOPS), 1 mM ethylenediaminetetraacetic acid (EDTA), 8 mM sodium acetate, and 2.2 M formaldehyde. After separation, the RNA was transferred to MSI nylon membrane (Micron Separations, Inc., Westborough, Mass.) for 18 hr. The RNA was pre-hybridized in Rapid-Hyb buffer (Amersham Life Science, Arlington Heights, Ill.) containing 100 μg/ml denatured salmon sperm DNA at 65° C. for 1 hour. Labeled probe ($^{32}$P-dCTP) was added and hybridized for 3 hr at 65° C. Membranes were washed twice with 2×SSPE/0.1% SDS for 15 min at 65° C., once with 1×SSPE/0.1% SDS at 42° C., twice with 0.1×SSPE/0.1% SDS at 42° C. The hybridization signal was detected by autoradiography (Kodak, Rochester, N.Y., OMAT film for 1 to 16 hr at −80° C.). $p21^{cip1}$ RNA was detected with a 2.1-kb probe, consisting of the NotI fragment from the pC-waf1-S plasmid described by El-Deiry et al. (31), as noted above. 18S rRNA was detected with a 1.15-kb probe, consisting of the BamHI-EcoRI fragment from the p5B plasmid described by Bowman et al. (15).

Western blots. Polyclonal or monoclonal antibody for $p21^{cip1}$ was obtained from Santa Cruz Biotechnology, Inc. (Santa Cruz, Calif.). Monoclonal antibodies against m-calpain, μ-calpain or calpastatin were generously provided by Dr. R. I. Mellgren (see also 75). Cells were harvested as described previously (18) by dislodging the cells with a cell lifter in phosphate buffered saline. The cells were collected by sedimentation and lysed in NP-40 lysis buffer [50 mM Tris, pH 7.4, 50 mM NaCl, 0.5% NP-40, and 1 mM $NaVO_3$, 50 mM NaF, 1mM phenylmethylsulfonyl fluoride (PMSF), 1 mM dithiothreitol (DTT), 25 μg/ml trypsin inhibitor, 25 μg/ml aprotinin, 1 mM benzamide, and 25 μg/ml pepstatin A added just before use]. Cellular debris was removed by sedimentation and the supernatant fluids were reserved. The protein concentration was determined by the BCA protein assay (Pierce, Rockford, Ill.). Whole cell extracts (40 μg/lane) were fractionated by SDS-polyacrylamide gel electrophoresis (PAGE), and the polypeptides were transferred to nitrocellulose membranes (Bio-Rad Laboratories, Hercules, Calif.) as described previously (18). Antigen-antibody reactions were detected with the enhanced chemiluminescent assay (Amersham Pharmacia Biotech) following the manufacturer's recommendations.

Measurement of intracellular calpain activity. Calpain activity was measured using the cell-permeant fluorogenic calpain substrate t-Boc-L-leucyl-L-methionineamide-7-amino-4-chloromethylcoumarin (Boc-Leu-Met-CMAC; Molecular Probes, Eugene, Oreg.). HCMV- or mock-infected cells were loaded with Boc-Leu-Met-CMAC (10 μM) for 15 min at selected times after infection. Afterwards, the cells were dissociated by gentle trypsinization and resuspended in PBS. After entering cells, Boc-Leu-Met-CMAC is conjugated to thiols, particularly glutathione, becoming impermeant for the plasmalemma. Cleavage of thiol-conjugated Boc-Leu-Met-CMAC by calpain releases thiol-conjugated 7-amino-4-methylcoumarin (AMC), unquenching the fluorescence. Thus, when cleavage is the rate-limiting step, the increase in fluorescence is proportional to the activity of the calpain (58). Fluorescence intensities of Boc-Leu-Met-CMAC-loaded cells were measured with a SLM 4800 spectrofluorometer. The relative fluorescence intensities were determined by measuring the fluorescence emission values at nm intervals from 390 nm to 550 nm, with excitation set at 380 nm, and the fluorescence signal was determined by integrating the area under the peak (at 460 nm). The time interval for loading the cells with Boc-Leu-Met-CMAC, harvesting the loaded cells, and measurement of fluorescence was constant for all samples.

Cleavage of $p21^{cip1}$ by calpain. Recombinant $p21^{cip1}$ was provided by Harper (37) or Ke (47), and was also prepared using the expression plasmid pET-p21 (37) according to the published methods (30). To evaluate the effect of calpains on $p21^{cip1}$, 400 ng of purified recombinant $p21^{cip1}$ was incubated with 0.004 units of either pure µ-calpain or m-calpain at 30° C. for 30 minutes in 40 µl of cleavage buffer, containing 25 mM Tris-HCl (pH 7.5), 100 mM NaCl, 3 mM DTT and 5 mM $CaCl_2$ (44). EDTA was added to 10 mM to stop the reaction. An equal volume of 2×SDS gel-loading buffer (18) was mixed with the digestion mixture and the mixture was immediately boiled for 5 min. The digestion products were evaluated by Western blot analysis or SDS-PAGE and coomassie brilliant blue staining.

Chemicals. The calpain inhibitors E64d [trans-epoxysuccinyl-L-leucylamido (4-guanidino)-butane] and Z-Leu-Leu-H were purchased from Peptides International, Inc. (Louisville, Ky.). Calpain II (m-calpain), penicillin, streptomycin, diethylpyrocarbonate, Tris, NaCl, $NaVO_3$, NaF, PMSF, DTT, trypsin inhibitor, aprotinin, benzamide, and pepstatin A were purchased from Sigma (St. Louis, Mo.). Calpain I (µ-calpain) and NP-40 were obtained from Calbiochem (San Diego, Calif.). Boc-Leu-Met-CMAC, and CMAC were purchased from Molecular Probes (Eugene, Oreg.).

EXAMPLE I

Comparison of $p21^{cip1}$ RNA and protein levels in HCMV-infected LU cells.

Figure 2:
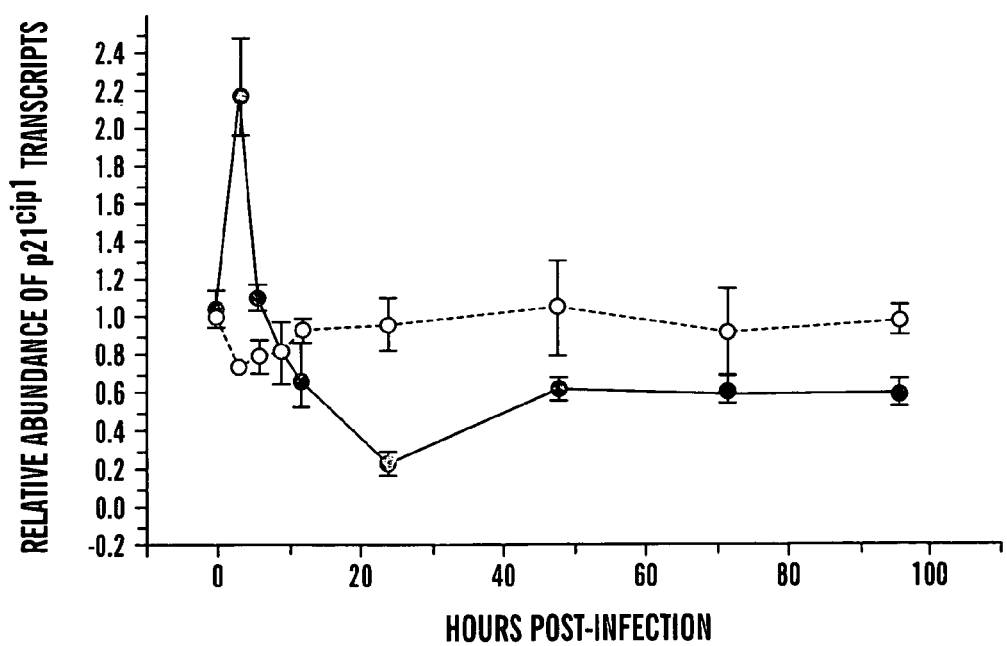
FIG. 2 illustrates the results shown in FIG. 1 evaluated by densitometric analysis and plotted as the abundance relative to the mock-infected control at 0 hr PI.
Figure 3:
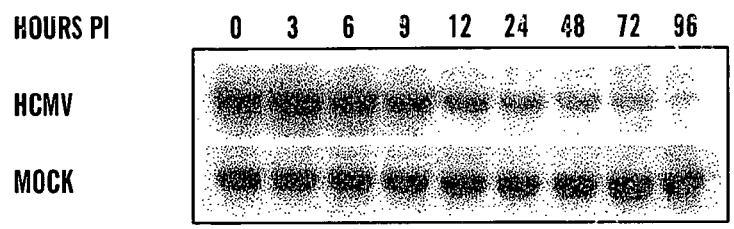
FIG. 3 is a Western blot showing the abundance of $p21^{cip1}$ after HCMV infection or mock infection.
Figure 4:
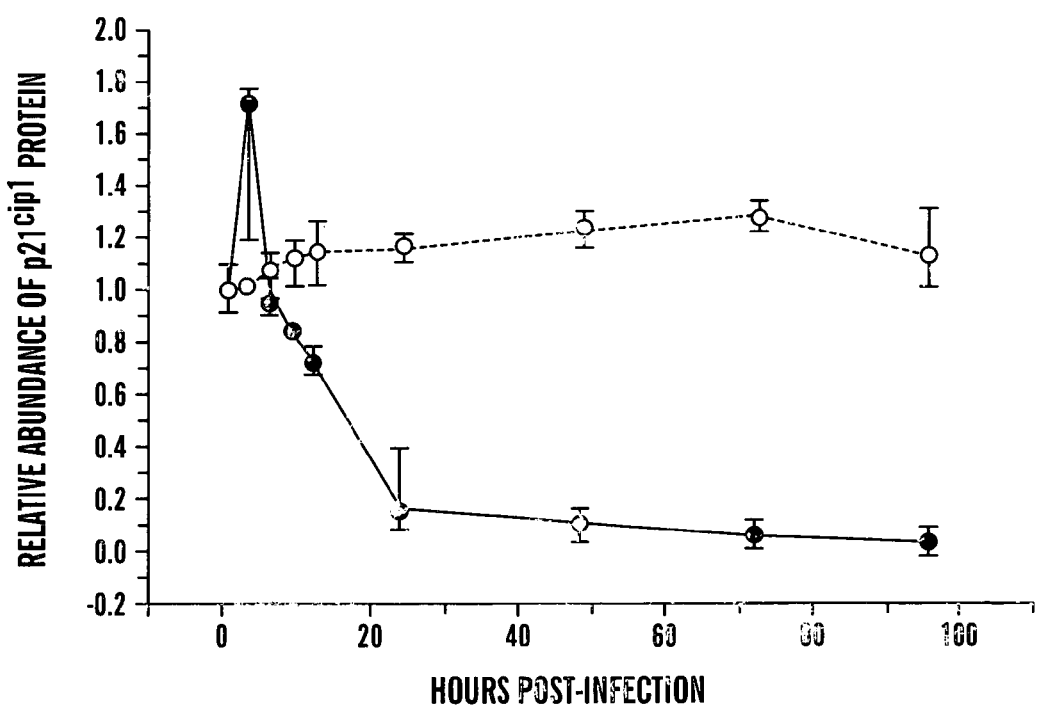
FIG. 4 illustrates the results shown in FIG. 3 evaluated by densitometric analysis and plotted as the abundance relative to the mock-infected control at 0 hr PI.

Previous studies demonstrated that HCMV infection caused a substantial decrease in the abundance of $p21^{cip1}$ protein in LU cells (18). To investigate the mechanism responsible for the decrease in $p21^{cip1}$ protein, the levels of $p21^{cip1}$ transcripts were measured by Northern blot analysis in density-arrested LU cells following stimulation with 10% fetal bovine serum (FBS). HCMV (5 PFU/cell) infection, or mock infection (FIGS. 1 and 2). In density-arrested cells, FBS or mock infection had little effect on $p21^{cip1}$ RNA levels. Following HCMV infection of density-arrested LU cells, $p21^{cip1}$ RNA levels increased briefly at 3 hr post-infection (PI), fell off dramatically thereafter, and then increased somewhat, beginning about 48 hr PI. Western blot analysis (FIGS. 3 and 4) demonstrated that $p21^{cip1}$ protein abundance did not altogether follow the observed changes in RNA levels. After an early increase at 3 hr PI, $p21^{cip1}$ protein abundance fell gradually, as had been observed previously (18). The disparity between $p21^{cip1}$ RNA and protein levels in the HCMV-infected cells, but not in mock-infected cells, suggested that $p21^{cip1}$ might be degraded differentially in HCMV- and mock-infected cells.

FIGS. 1-4. 1 and 2. Northern blot: 1. The effect of HCMV infection (HCMV), serum growth factors (Serum), or mock infection (Mock) on RNA levels for $p21^{cip1}$ in density-arrested LU cells. The arrested cells were infected at a multiplicity of 5 PFU/cell, exposed to fresh fetal bovine serum (10%), and mock-infected. RNA was isolated at the times indicated in the Fig., and 20 µg of RNA from each lysate was resolved by formaldehyde denaturing agarose gel electrophoresis. The RNA was transferred to nylon membranes and evaluated by Northern blot analysis. Ribosomal 18s RNA (18S) was used as a loading standard. 2: The results illustrated in FIG. 1 were evaluated by densitometric analysis and plotted as the abundance relative to the mock-infected control at 0 hr PI (-●-, $p21^{cip1}$ RNA, HCMV-infected cells; -○-, $p21^{cip1}$ RNA, mock-infected cells). 3 and 4. Western blot: 3. The abundance of $p21^{cip1}$ after HCMV infection or mock infection. Parallel cultures of density-arrested LU cells were treated as in the legend to FIG. 1. Whole cell lysates were prepared at the indicated intervals, and 40 µg of protein from each was resolved by SDS-PAGE. The proteins were transferred to nitrocellulose membrane and probed with antibodies against $p21^{cip1}$.4: The results illustrated in FIG. 3 were evaluated by densitometric analysis and plotted as the abundance relative to the mock-infected control at 0 hr PI (-●-, $p21^{cip1}$ protein, HCMV-infected cells; -○-, $p21^{cip1}$ protein, mock-infected cells).

EXAMPLE II

Differential effects of inhibitors of the ubiquitin/proteasome proteolytic pathway on $p21^{cip1}$ degradation during HCMV infection and mock infection.

Figure 5:
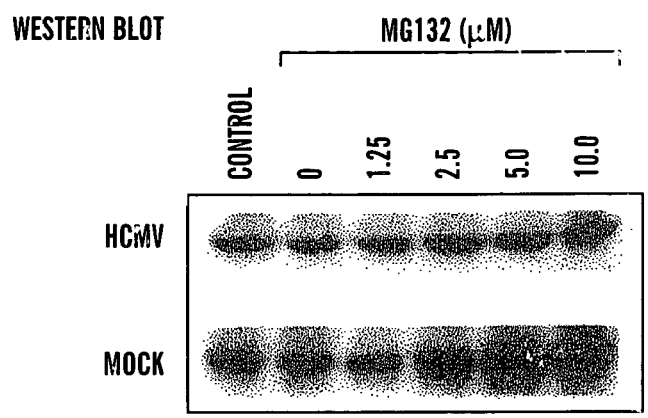
FIG. 5 illustrates the effect of MG132, an inhibitor of proteasome degradation, on $p21^{cip1}$ abundance in HCMV- or mock-infected, density-arrested LU cells.
Figure 6:
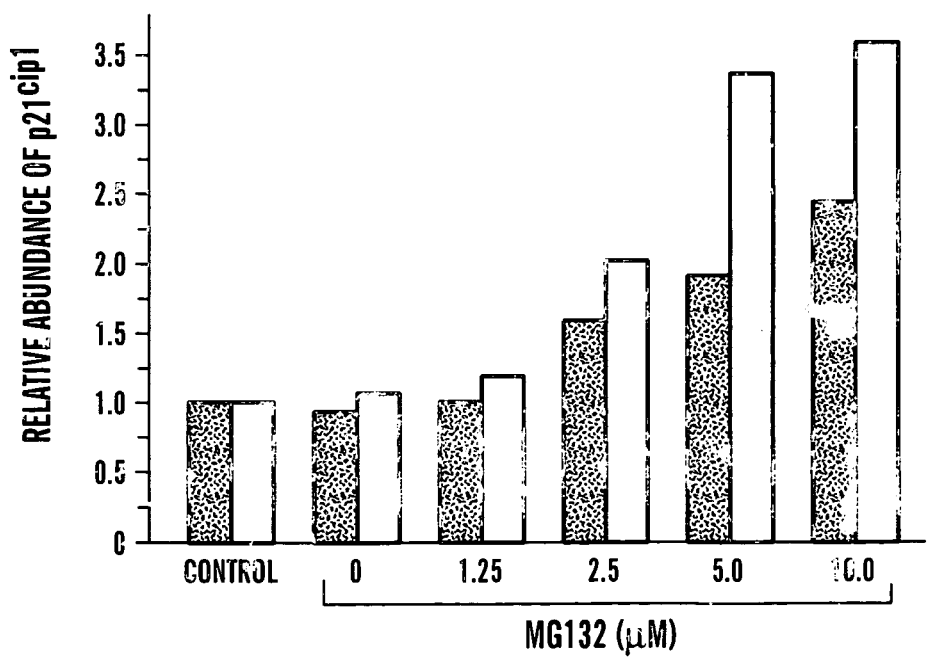
FIG. 6 illustrates the abundance of $p21^{cip1}$ after MG132 treatment determined by densitometry of the data illustrated in FIG. 5.

Since the ubiquitin/proteasome pathway is reported to be responsible for degrading many of the cell cycle regulatory proteins, the decrease of $p21^{cip1}$ in HCMV-infected cells could have been due to a proteasome-mediated mechanism. Indeed, the proteasome inhibitor MG132 (49,60) stabilized $p21^{cip1}$ in mock-infected, density-arrested LU cells, but had only a limited effect on stabilization of $p21^{cip1}$ in HCMV-infected cells (FIGS. 5 and 6). Mock-infected, density-arrested LU cells treated with MG132 (0 to 10 µM) immediately after mock infection and harvested at 24 hr, when $p21^{cip1}$ levels were declining in HCMV-infected cells (FIGS. 1-4, and reference 18), demonstrated a concentration-dependent increase in the abundance of $p21^{cip1}$. A 3.6-fold increase in $p21^{cip1}$ abundance relative to either the dimethylsulfoxide (DMSO) solvent control or cells in the absence of any chemical was observed at a concentration of 10 µM (FIGS. 5 and 6). In parallel, in HCMV (5 PFU/ml)-infected cells, smaller increases in $p21^{cip1}$ abundance were observed at MG132 concentrations from 2.5 µM to 10 µM. That the $p21^{cip1}$ abundance was less responsive to protection by MG132 in HCMV-infected cells than in mock-infected cells is demonstrated by the difference in the slopes (determined by linear regression analysis) of the concentration effect of MG132 in HCMV-infected (0.19, p<0.01) and mock-infected (0.33, p<0.01) cells. These findings suggest that additional MG132-insensitive pathway(s) may be involved in the proteolysis of $p21^{cip1}$ in HCMV-infected cells. The unidentified mechanism(s) seemed to be quantitatively more important in $p21^{cip1}$ proteolysis in HCMV-infected cells than was proteasome-mediated degradation, and therefore there was an interest in identifying the proteolytic mechanism(s) stimulated by HCMV infection.

FIGS. 5 and 6. The effect of MG132, an inhibitor of proteasome degradation, on $p21^{cip1}$ abundance in HCMV- or mock-infected, density-arrested LU cells. 5. LU cells were density arrested, as described in Materials and Methods. The cell cultures were HCMV (5 PFU/cell)- or mock-infected and then exposed to selected concentrations of MG132 at 24 hr PI. Cell lysates were prepared at 30 hr PI (i.e., 6 hr after E64d treatment), and 40 µg of protein from each lysate was resolved by SDS-PAGE. The proteins were transferred to nitrocellulose and probed with antibodies against $p21^{cip1}$. Control, cells cultured in the absence of MG132 or its solvent, DMSO. 0, DMSO solvent control, consisting of cells treated with the same concentration of DMSO (0.1%) present in the cultural fluids containing highest concentration of MG132 (10 µM). 6. Represents the abundance of $p21^{cip1}$ after MG132 treatment determined by densitometry of the data illustrated in FIG. 5. The data for mock-infected cells (open bars) were calculated relative to the $p21^{cip1}$ abundance in untreated mock-infected cells, while the data for HCMV-infected cells (closed bars) were determined relative to the $p21^{cip1}$ abundance in untreated HCMV-infected cells.

EXAMPLE III

Calpain inhibitors, E64d and Z-Leu-Leu-H, protect $p21^{cip1}$ from degradation during HCMV infection.

Figure 7:
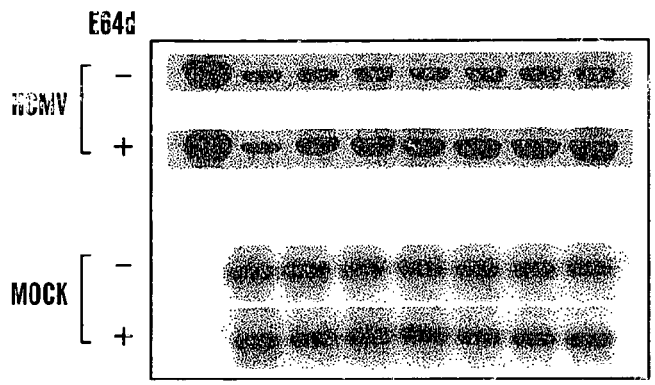
FIG. 7 illustrates the cumulative effect of the calpain inhibitor E64d on $p21^{cip1}$ protein levels in HCMV- or mock-infected density-arrested LU cells.
Figure 8:
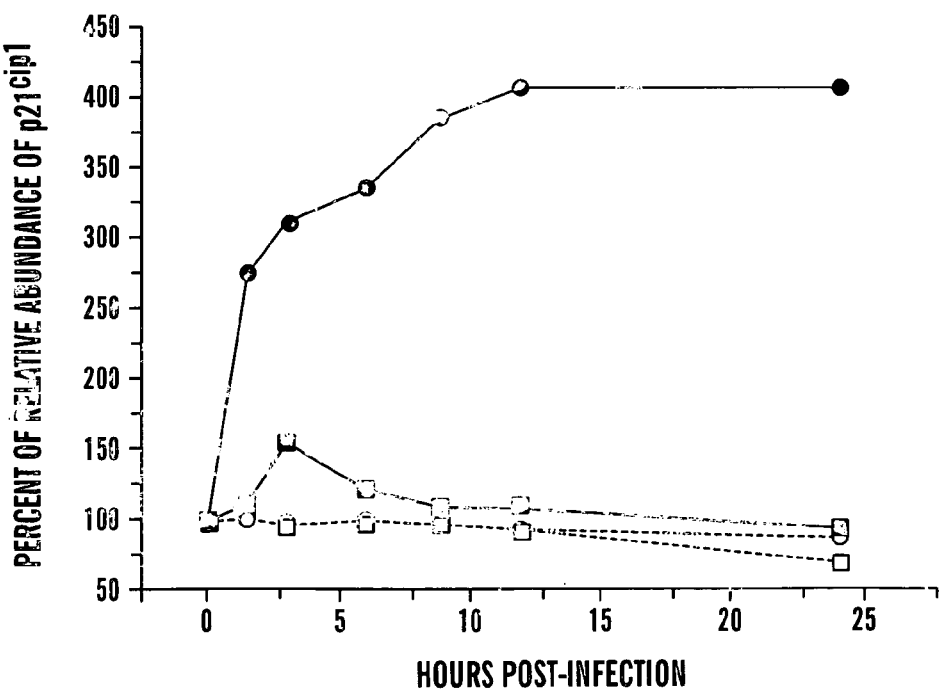
FIG. 8 illustrates the accumulation of $p21^{cip1}$ after E64d treatment determined by densitometry of the data illustrated in FIG. 7.

HCMV infection induces a substantial increase in $[Ca^{2+}]_i$ and in phospholipid degradation, raising the possibility that $Ca^{2+}$-activated neutral proteases (calpains) might be activated by HCMV infection and participate in the proteolysis of $p21^{cip1}$. Previous work has demonstrated that calpains are able to cleave some cell cycle regulatory proteins, such as cyclin $D_1$, cellular oncogene products (e.g., c-Mos, c-Jun and c-Fos), and p53 (39,52; for review, see 20,26). The possibility that calpain-mediated proteolysis was involved in the degradation of $p21^{cip1}$ in HCMV-infected cells was first investigated by examining the effect of the calpain inhibitors E64d (68) and Z-Leu-Leu-H (60) on $p21^{cip1}$ levels following HCMV infection. In the initial experiments, the effect of E64d (100 μM) on $p21^{cip1}$ levels was examined by Western blot analysis beginning at 48 hr PI, when $p21^{cip1}$ is at or near its lowest level (FIGS. 1-4; and reference 18) in HCMV-infected (5 PFU/cell), density-arrested LU cells. The abundance of $p21^{cip1}$ was determined at selected intervals for 24 hr following treatment with E64d (FIGS. 7 and 8). As noted previously, a substantial decrease in $p21^{cip1}$ levels was observed at 48 hr PI in HCMV-infected cells just prior to treatment with E64d (FIGS. 7 and 8, compare lanes 1 and 2 in FIG. 7 for HCMV-infected cells). Except at 3 hr post-treatment with E64d, when there was about a 56% increase in $p21^{cip1}$ in the presence of E64d, the calpain inhibitor had little, if any, effect on the abundance of $p21^{cip1}$ in mock-infected density-arrested LU cells. In contrast, in HCMV-infected cells in the presence of E64d, a substantial accumulation of $p21^{cip1}$ was observed. A 4-fold increase in the abundance of $p21^{cip1}$ in HCMV-infected cells was observed after 12 hr of E64d treatment, while in the absence of E64d levels of $p21^{cip1}$ remained at a relatively constant low level. The maximum level of $p21^{cip1}$ in the E64d-treated cells under these conditions was about 84% of that observed at 0 hr. These data suggest that an E64d-sensitive proteolytic pathway is induced in HCMV-infected cells and is largely responsible for a substantial decrease in the abundance of $p21^{cip1}$.

Figure 9:
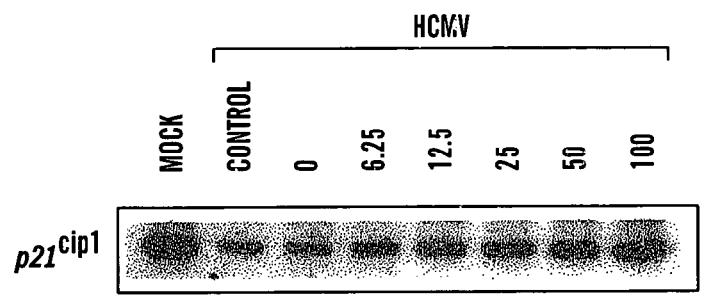
FIG. 9 illustrates the concentration effect of E64d on $p21^{cip1}$ abundance in HCMV-infected cells.
Figure 10:
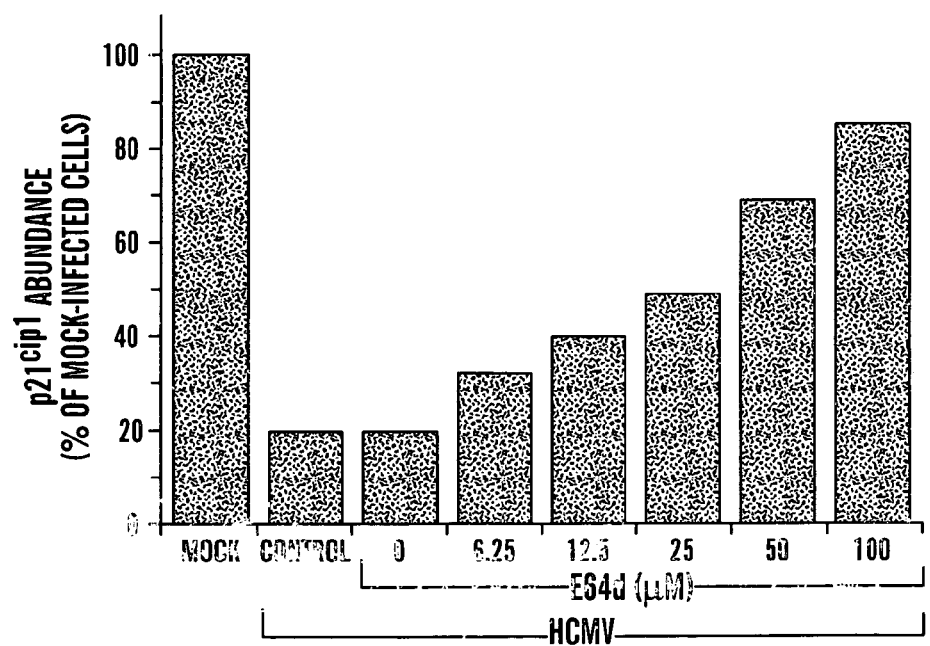
FIG. 10 illustrates the abundance of $p21^{cip1}$ determined by densitometric analysis of the data in FIG. 9.

The concentration effect of E64d on $p21^{cip1}$ abundance was examined in HCMV (5 PFU/cell)-infected density-arrested LU cells. Protection of $p21^{cip1}$ was directly dependent on the concentration of E64d (FIGS. 9 and 10). Protection of $p21^{cip1}$ was observed at all concentrations evaluated (6.25 to 100 μM), with the cells treated with the highest concentration of E64d (100 μM) demonstrating about 85% of the abundance measured in mock-infected cells over the same time period. As described above (FIGS. 7 and 8), E64d had little, if any, effect on $p21^{cip1}$ levels in mock-infected cells even at a concentration of 100 μM. Z-Leu-Leu-H also protected $p21^{cip1}$ in a concentration-dependent manner in HCMV (5 PFU/cell)-infected, density-arrested LU cells (FIGS. 11 and 12), with some protection by all concentrations of Z-Leu-Leu-H evaluated. The levels of protection provided by Z-Leu-Leu-H were similar to those observed with E64d (FIGS. 9 and 10). A concentration of 100 μM of Z-Leu-Leu-H resulted in about 72% of the mock-infected levels of $p21^{cip1}$ compared to 85% for cells treated with E64d.

Figure 13:
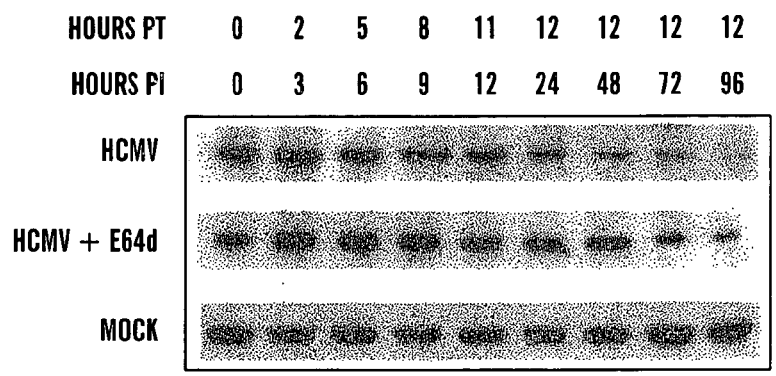
FIG. 13 illustrates the time course for the effect of E64d on $p21^{cip1}$ abundance in HCMV-infected, density-arrested cells.
Figure 14:
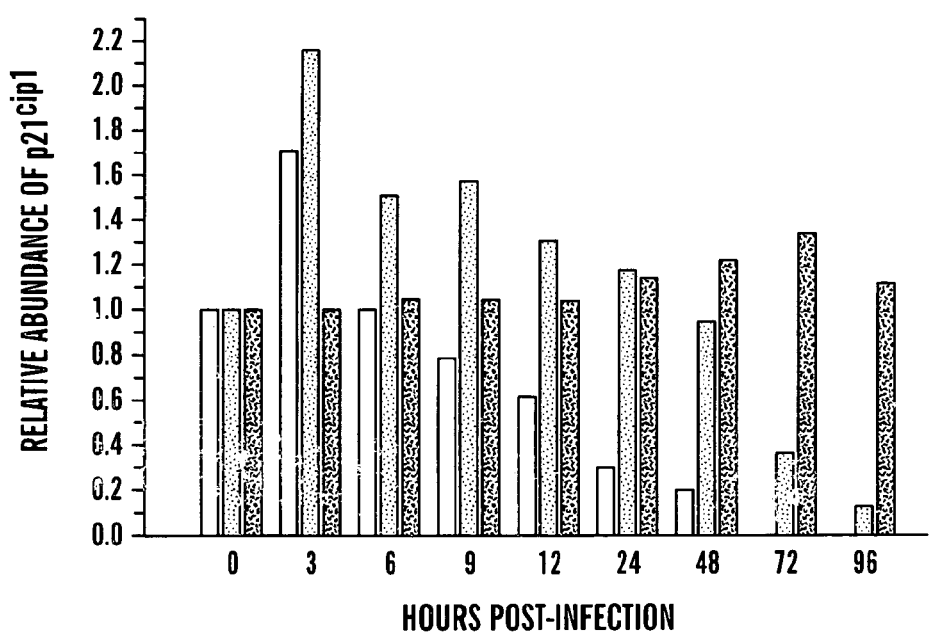
FIG. 14 illustrates the abundance of $p21^{cip1}$ determined by densitometric analysis of the data shown in FIG. 13.

To determine the effect of E64d (100 μM) on $p21^{cip1}$ levels throughout the time course of HCMV infection, density-arrested LU cell cultures were either HCMV- or mock-infected and treated with E64d up to 12 hr before harvest. For cells harvested at 12 hr PI or before, the cells were treated with E64d from 1 hr PI to the time of harvest (FIGS. 13 and 14). E64d had little effect on $p21^{cip1}$ levels in mock-infected cells, as previously noted (FIGS. 7 and 8). In the absence of E64d, $p21^{cip1}$ levels in HCMV-infected cells increased at 3 hr and dropped off by 6 hr (FIGS. 13 and 14). By 72 hr PI, $p21^{cip1}$ was not detectable in the HCMV-infected cells in the absence of E64d. In the presence of E64d, $p21^{cip1}$ levels in HCMV-infected cells were consistently greater (from 3 hr to 96 hr PI) than the levels observed in the absence of the calpain inhibitor. As a result of E64d treatment, $p21^{cip1}$ levels remained at or above the pre-infection levels and levels in mock-infected cells through 24 hr PI. After 48 hr, $p21^{cip1}$ levels in E64d-treated, HCMV-infected cells remained well above the levels in the absence of the calpain inhibitor, but the $p21^{cip1}$ abundance dropped progressively below the pre-infection levels. Considered together, these data suggest that calpain-mediated proteolysis contributes substantially to the degradation of $p21^{cip1}$ in HCMV-infected cells from 3 hr through the late phase of HCMV infection.

FIGS. 7 and 8. The cumulative effect of the calpain inhibitor E64d (100 μM) on $p21^{cip1}$ protein levels in HCMV- or mock-infected density-arrested LU cells. 7: LU cells were arrested by contact inhibition as described in Materials and Methods. The cells were HCMV (5 PFU/cell)- or mock-infected and then exposed to E64d at 48 hr PI.

At the times indicated in the FIG., whole cell lysates were prepared, and 40 μg of protein from each lysate was analyzed by SDS-PAGE. The proteins were transferred to nitrocellulose and probed with antibodies against $p21^{cip1}$. Hours PT (post-treatment) indicates the duration of E64d exposure. Hours PI indicates the time of harvest after infection. Note that the exposure time for blots of lysates from HCMV-infected cells was about three times longer than that required for blots of lysates from mock-infected cells. Accordingly, lane 1 for the HCMV-infected cell lysates was loaded with lysates from mock-infected cells treated or not treated with E64d. 8. Represents the accumulation of $p21^{cip1}$ after E64d treatment determined by densitometry of the data illustrated in FIG. 7. The data for $p21^{cip1}$ abundance in HCMV- and mock-infected cells are plotted relative to the $p21^{cip1}$ abundance at 0 hr in the absence of E64d in HCMV- or mock-infected cells, respectively (-□-, mock-infected cells; -○-, mock-infected cells treated with E64d; -■-, HCMV-infected cells; -●-, HCMV-infected cells treated with E64d).

FIGS. 9 and 10. The concentration effect of E64d on $p21^{cip1}$ abundance in HCMV-infected cells. 9: LU cells were density arrested as described in Materials and Methods. The cells were HCMV (5 PFU/cell) or mock infected, and at 48 hr PI were treated with selected concentrations of E64d. Whole cell lysates were prepared 6 hr later, and 40 μg of protein from each lysate was resolved by SDS-PAGE. The proteins were transferred to nitrocellulose and probed with antibodies to $p21^{cip1}$. Mock: mock-infected cells in the absence of drug. Control, untreated HCMV-infected cells. 0, DMSO solvent control, consisting of HCMV-infected cells treated with the same concentration of DMSO solvent (0.1%) contained in the highest concentration of E64d. 10:

Represents the abundance of p21$^{cip1}$ determined by densitometric analysis of the data in FIG. 9.

Figure 11:
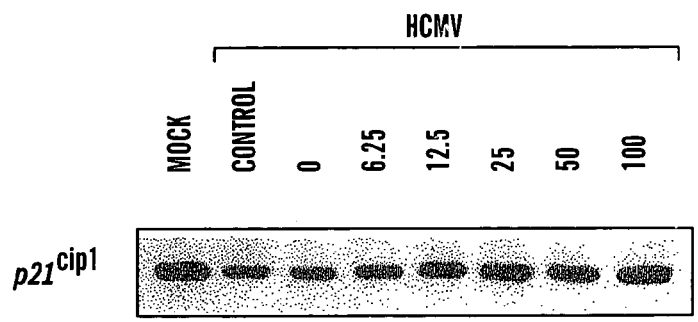
FIG. 11 illustrates the concentration effect of Z-Leu-Leu-H on $p21^{cip1}$ abundance in HCMV-infected cells.
Figure 12:
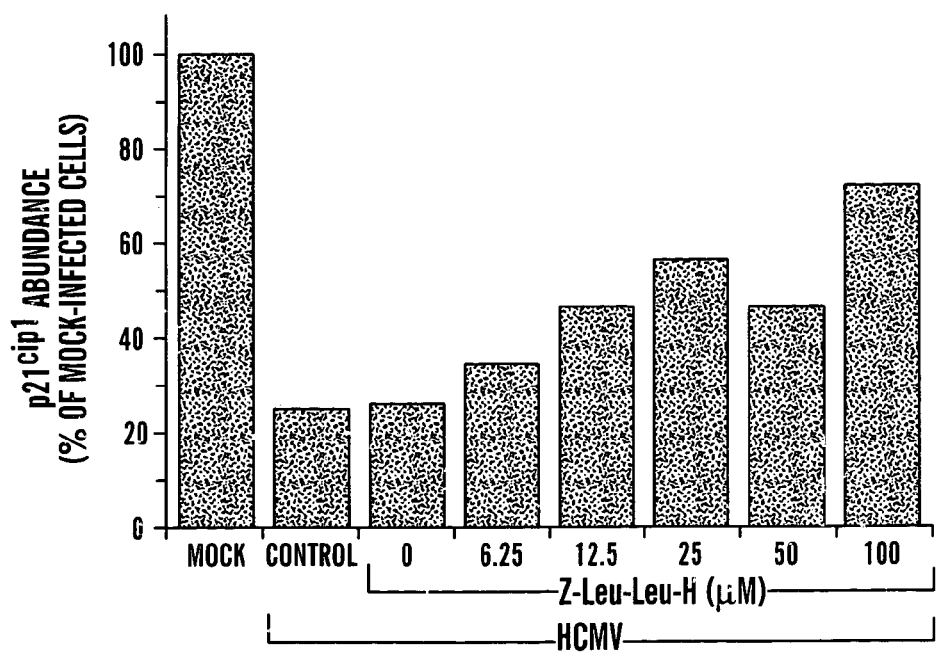
FIG. 12 illustrates the abundance of $p21^{cip1}$ determined by densitometric analysis of the data in FIG. 11.

FIGS. 11 and 12. The concentration effect of Z-Leu-Leu-H on p21$^{cip1}$ abundance in HCMV-infected cells. 11. LU cells were density arrested as described in Materials and Methods. The cells were HCMV (5 PFU/cell) infected, and at 48 hr PI were treated with selected concentrations of Z-Leu-Leu-H. Whole cell lysates were prepared 6 hr later, and 40 μg of protein from each lysate was resolved by SDS-PAGE. The proteins were transferred to nitrocellulose and probed with antibodies to p21$^{cip1}$. Mock, Control, and 0 are defined as in the legend to FIG. 9. 12 : Represents the abundance of p21$^{cip1}$ determined by densitometric analysis of the data in FIG. 11.

FIGS. 13 and 14. The time course for the effect of E64d on p21$^{cip1}$ abundance in HCMV-infected, density-arrested cells. 13: LU cells were density arrested, as described in Materials and Methods. The cells were HCMV (5 PFU/cell) or mock infected, and at the intervals indicated in the Fig., beginning 1 hr after infection, subsets of the cells were treated with E64d (100 μM). Whole cell lysates were prepared at the times indicated in the Fig. [up to 12 hr after treatment (PT)], and 40 μg of protein from each lysate was resolved by SDS-PAGE. The proteins were transferred to nitrocellulose and probed with antibodies to p21$^{cip1}$ 14. Represents the abundance of p21$^{cip1}$ determined by densitometric analysis of the data shown in FIG. 13. Open bars, HCMV-infected cells. Diagonally stripped bars, HCMV-infected cells treated with E64d. Cross-hatched bars, mock-infected cells.

EXAMPLE IV

Calpain is activated by HCMV infection.

The level of calpain activity is normally very low in unstimulated cells due to the presence of the endogenous calpain inhibitor calpastatin (20). The findings that treatment of HCMV-infected cells with E64d or Z-Leu-Leu-H led to stabilization and accumulation of p21$^{cip1}$ in HCMV-infected cells suggested that calpain may be activated during HCMV infection. To investigate this possibility, calpain activity was measured in density-arrested LU cells using the fluorogenic calpain substrate Boc-Leu-Met-CMAC (58). Calpain-mediated cleavage of this substrate generates 7-amine-4-methylcoumarin (AMC) and unquenches the fluorescence of the molecule, providing a sensitive assay of intracellular calpain activity. Density-arrested LU cells were HCMV (5 PFU/cell) or mock infected, and 15 min before assay, exposed to Boc-Leu-Met-CMAC (10 μM). The cells were harvested as detailed in Materials and Methods, and the relative fluorescence determined using a SLM4800S spectrofluorometer. The data, summarized in FIG. 15, demonstrate that AMC fluorescence fell in mock-infected cells during the course of these experiments. HCMV infection, however, induced a substantial increase in calpain activity. An increase in AMC fluorescence was observed by 6 hr PI. After 24 hr, the fluorescence of HCMV-infected cells increased to a value about 8-fold greater than that observed in mock-infected cells. The relative fluorescence in the HCMV-infected cells increased further at 48 hr PI. These data closely reflect the time course for the changes in the abundance of p21$^{cip1}$ following HCMV infection in earlier work (18) and in this study. In these studies, a decrease in p21$^{cip1}$ levels was first detected at 6 hr PI, and the abundance of p21$^{cip1}$ continued to decrease through 48 hr PI.

Figure 15:
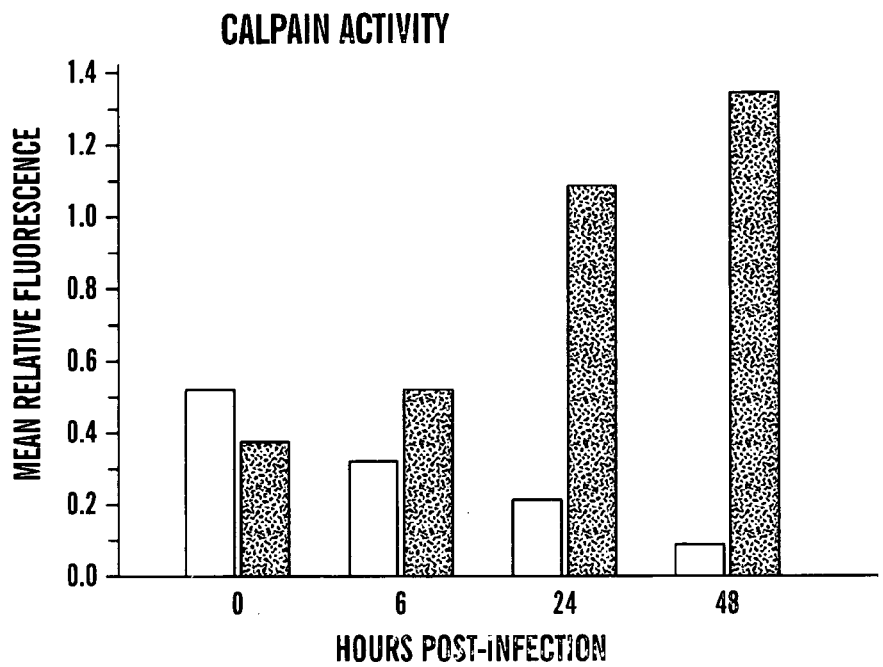
FIG. 15 illustrates the time course for calpain activity in HCMV-infected and mock-infected, density-arrested cells.

To determine if the increased calpain activity observed in FIG. 15 was a result of increased expression of calpains or a decrease in the abundance of calpastatin, the abundance of these molecules was measured by Western blot analysis in cells treated in parallel with those used to measure calpain activity. HCMV infection had little effect on the abundance of μ-calpain (FIG. 16), m-calpain (FIG. 17), or calpastatin (FIG. 18) through 24 hr PI. Beginning at 48 hr, m-calpain levels declined slightly in HCMV-infected cells. Calpastatin and μ-calpain levels were unaffected by HCMV or mock infection. Thus, it is unlikely that the increase in calpain activity is a result of a decrease in calpastatin abundance or an increase in the abundance of the ubiquitous calpains.

Figure 16:
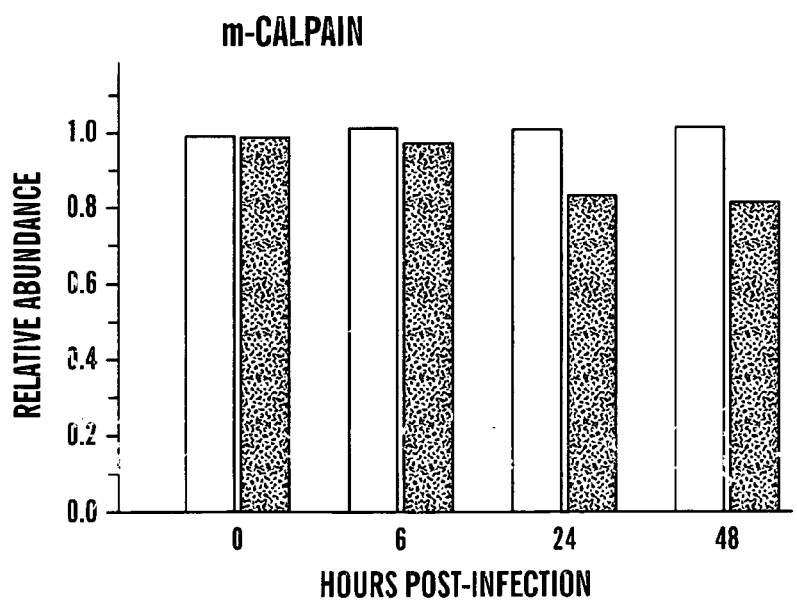
FIG. 16 illustrates the abundance of m-calpain in parallel cell cultures determined by densitometric analysis of Western blots.
Figure 17:
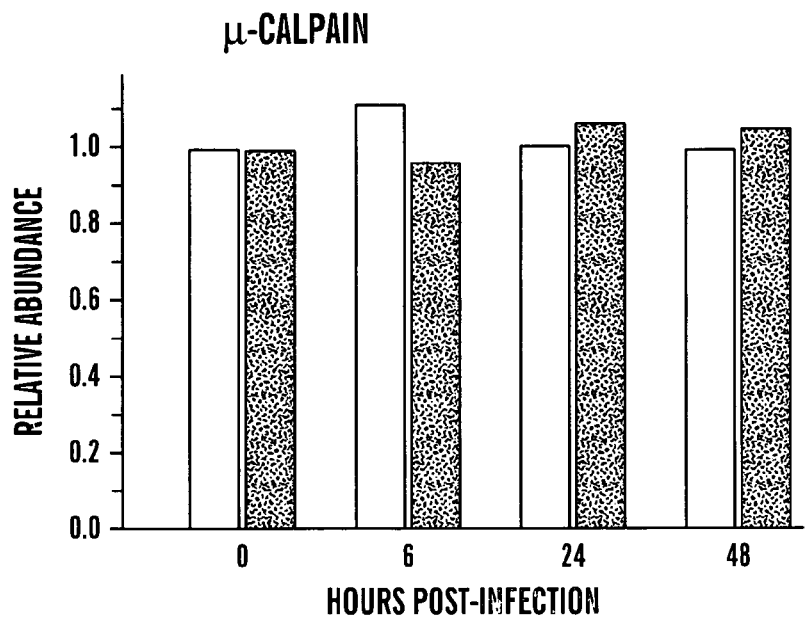
FIG. 17 illustrates the abundance of μ-calpain in parallel cell cultures determined by densitometric analysis of Western blots.
Figure 18:
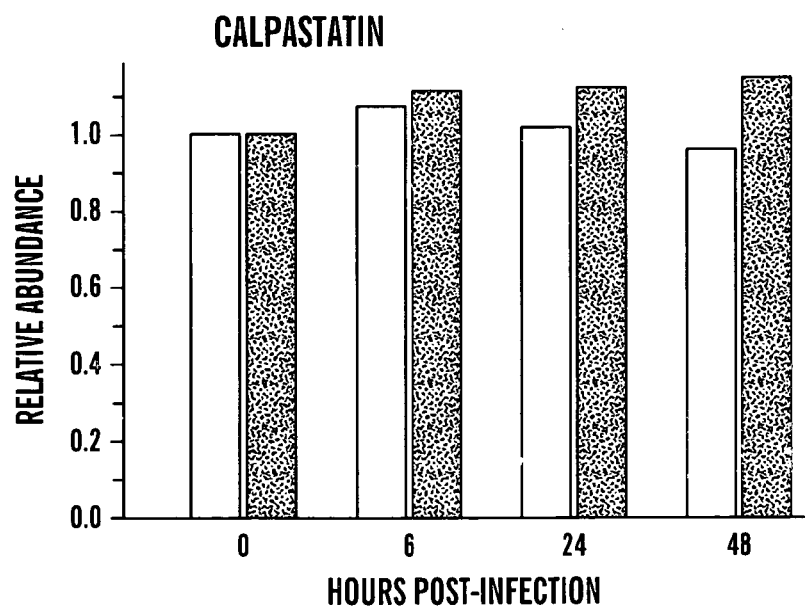
FIG. 18 illustrates the abundance of calpastatin in parallel cell cultures determined by densitometric analysis of Western blots.

FIGS. 15-18. 15. The time course for calpain activity in HCMV (5 PFU/cell)-infected (solid bars) and mock-infected (open bars) density-arrested cells. Calpain activity was measured by exposing the cells to the cell permeant fluorogenic calpain substrate Boc-Leu-Met-CMAC (18 μM) for 15 minutes before the fluorescence intensity was measured for equal numbers of HCMV- and mock-infected cells using an SLM 4800S spectrofluorometer. Excitation was at 380 nm, emission was at 460 nm. The polarizers were set at 0° and 50°. FIGS. 16, 17 and 18 illustrate the abundance of m-calpain, μ-calpain, and calpastatin, respectively, in parallel cell cultures determined by densitometric analysis of Western blots.

EXAMPLE V

Calpain cleaves p21$^{cip1}$.

Figure 19:
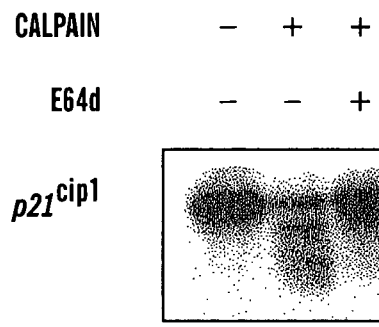
FIG. 19 is a Western blot illustrating the cleavage of purified recombinant $p21^{cip1}$ by purified μ-calpain in the presence or absence of E64d.

The number of proteins recognized as targets of calpain-mediated proteolysis has increased substantially during the last decade (20). Nevertheless, p21$^{cip1}$ has not been previously identified as a potential target of calpain. Accordingly, there was an interest in directly testing the sensitivity of p21$^{cip1}$ to calpain-mediated proteolysis by incubating purified recombinant p21$^{cip1}$ (37 or 47), with either purified μ-calpain or m-calpain and evaluating the products by Western blot analysis. Recombinant p21$^{cip1}$ was also prepared using the expression plasmid pET-p21 (37,30). Incubation of any of the purified p21$^{cip1}$ preparations with purified μ-calpain or m-calpain resulted in the rapid cleavage of p21$^{cip1}$, as illustrated in FIG. 19 for μ-calpain. Two prominent p21$^{cip1}$ fragments were observed after incubation with calpain, consistent with the results from earlier studies indicating that calpain often cleaves its target proteins at a limited number of sites (for a review, see 67). Inclusion of E64d in the digestion inhibited the proteolysis of p21$^{cip1}$ as shown in FIG. 19. To investigate if calpain were removing or modifying the availability of the epitope that was the target of the anti-p21$^{cip1}$ antibody used in the Western blot analysis, p21$^{cip1}$ and casein [a well-established target of calpain-mediated degradation (74)] were incubated separately with either μ-calpain or m-calpain and the proteolytic products were examined by PAGE. The location of polypeptides in the gels was demonstrated by coomassie brilliant blue staining. In order to minimize the loss of small peptides electrophoresis of protein applied to these gels was for a shorter period of time than those used for Western blot analysis (FIG. 19). A limited number of cleavage products was observed in the coomassie blue-stained gels (FIG. 20), as had been observed by Western blot analysis (FIG. 19). Thus, p21$^{cip1}$ appears to be a target for calpain-mediated proteolysis. Considered together, these data suggest that calpain activation contributes substantially to the overall reduction of p21$^{cip1}$ abundance and, thus, in cell cycle progression in HCMV-infected cells.

Figure 20:
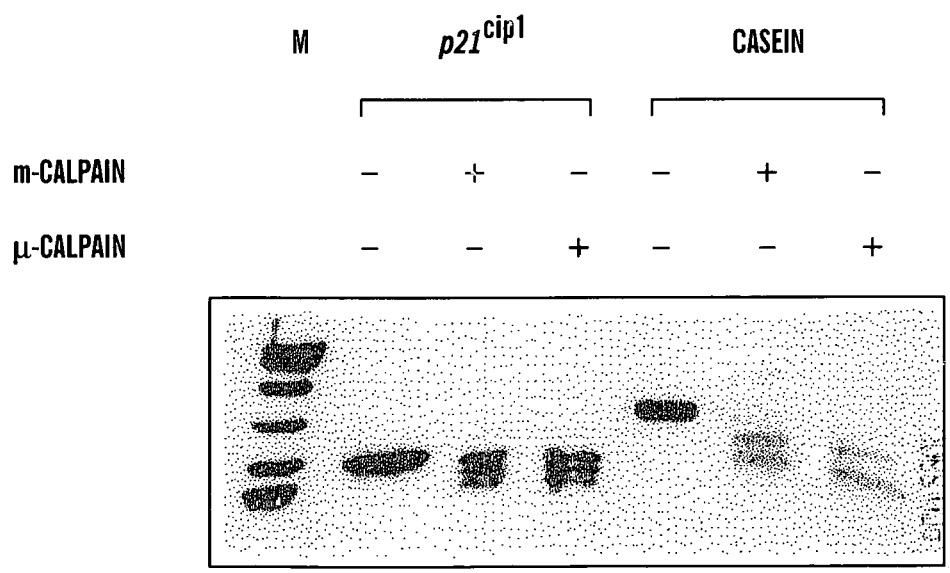
FIG. 20 is an SDS-PAGE illustrating the cleavage of purified recombinant $p21^{cip1}$ or casein by μ-calpain or m-calpain.

FIGS. 19 and 20. Cleavage of purified recombinant p21$^{cip1}$ by purified ubiquitous calpains. 19. p21$^{cip1}$ (0.4 μg)

was incubated with µ-calpain (0.004 units) for 30 min at 30° C. in the presence or absence of E64d (100 µM) and the resulting products were analyzed by Western blot analysis, as described in Materials and Methods 20. p21$^{cip1}$ (4 µg) or casein (3 µg) was incubated with 0.04 units of µ-calpain or m-calpain for 30 min at 30° C. and the products of the digestion were examined by SDS-PAGE and coomassie brilliant blue staining. M: Rainbow™ colored protein molecular weight markers of 97.4, 66, 46, 30, 21.5, and 14.3 kDa (Amersham Life Science).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

1. AbuBakar et al., Arch Virol 113:255-266 (1990).
2. AbuBakar et al., Biochem Biophys Res Commun 166: 953-959 (1990).
3. Albrecht and Weller, Am J Clin Pathol 73:648-654 (1980).
4. Albrecht et al., J Invest Dermatol 98 (Suppl):29S-35S (1992).
5. Albrecht et al., Subcell Biochem 15:157-202 (1989).
6. Albrecht et al., Lab Invest 42:1-7 (1980).
7. Albrecht et al., J Gen Virol 30:167-177 (1976).
8. Alford et al., Rev Infect Dis 12 (Suppl): S745-S753 (1990).
9. not used
10. Blagosklonny et al., Biochem Biophys Res Commun 227:564-569 (1996).
11. Boldogh et al., Science 247:561-564 (1990).
12. Boldogh et al., J Virol 65:1568-1571 (1991).
13. Boldogh et al., Arch Virol 118:163-177 (1991).
14. Boldogh et al., Biochem Biophys Res Commun 197: 1505-1510 (1993).
15. Bowman et al., Nuc Acids Res 9:4951-4966 (1981).
16. Bresnahan et al., J Biol Chem 273:22075-22082 (1998).
17. Bresnahan et al., Virology 231:239-247 (1997).
18. Bresnahan et al., Virology 224:150-160 (1996).
19. Bresnahan et al., J Gen Viral 78:1993-1997 (1997).
20. Carafoli and Molinari, Biochem Biophys Res Commun 247:193-203 (1998).
21. not used
22. Chen et al., Oncogene 11:1931-1937 (1995).
23. Chomczynski, Biotechniques 15:532-534 (1993).
24. Ciechanover, Cell 79:13-21 (1994).
25. not used
26. Croall and DeMartino, Physiol Rev 71:813-847 (1991).
27. de Jong et al., Antiviral Res 39:141-162 (1998).
28. Dittmer and Mocarski, J Virol 71:1629-1634 (1997).
29. not used
30. Dynlacht et al., Methods Enzymol 283:230-244 (1997).
31. El-Deiry et al., Cell 75:817-825 (1993).
32. not used
33. Elledge and Harper, Biochim Biophys Acta 1377:M61-M70 (1998).
34. Flores-Rozas et al., Proc Natl Acad Sci USA 91:8655-8659 (1994).
35. Fukuchi et al., Biochim Biophys Acta 1404:405-411 (1998).
36. Gervais et al., J Biol Chem 273:19207-19212 (1998).
37. Harper et al., Cell 75:805-816 (1993).
38. Harper et al., Mol Cell Biol 6:387-400 (1995).
39. Hirai et al., FEBS Lett 287:57-61 (1991).
40. not used
41. Jault et al., J Virol 69:6697-6704 (1995).
42. Kearsey et al., Oncogene 11:1675-1683 (1995).
43. not used
44. not used
45. Li et al., Nature 371:534-537 (1994).
46. Lu and Shenk, J Virol 70:8850-8857 (1996).
47. Mayrose et al., Protein Sci 5:1928-1930 (1996).
48. not used
49. Murray et al., Exp Cell Res 242:460-469 (1998).
50. Noda et al., Exp Cell Res 211:90-98 (1994).
51. Nokta et al., Virology 157:259-267 (1987).
52. Pahl and Baeuerle, Curr Opin Cell Biol 8:340-347 (1996).
53. Pan et al., J Biol Chem 270:22008-22016 (1995).
54. Perez, Microbiologia 13:343-352 (1997).
55. Podust et al., Biochemistry 34:8869-8875 (1995).
56. not used
57. not used
58. Rosser et al., J Biol Chem 268:23593-23600 (1993).
59. Rubin, Rev Infect Dis 12(Suppl):S754-S766 (1990).
60. Saito et al., Neurosci Lett 120:1-4 (1990).
61. Santella, Biochem Biophys Res Commun 244:317-324 (1998).
62. Santella et al., Cell Calcium 23:123-130 (1998).
63. Schooley, Rev Infect Dis 12(Suppl):S811-S819 (1990).
64. not used
65. not used
66. not used
67. Suzuki and Sorimachi, FEBS Lett 433:1-4 (1998).
68. Tamai et al., J Pharmacobiodyn 9:672-677 (1986).
69. Valyi-Nagy et al., Arch Virol 101:199-207 (1988).
70. Waga et al., Nature 369:574-578 (1994).
71. Xiong et al., Nature 366:701-704 (1993).
72. Yu et al., Proc Natl Acad Sci USA 95:11324-11329 (1998).
73. Zhang et al., Genes Dev 8:1750-1758 (1994).
74. Zhang and Mellgren, Biochem Biophys Res Commun 227:891-896 (1996).
75. Zhang et al., J Biol Chem 271:18825-18830 (1996).
76. Zhu et al., Proc Natl Acad Sci USA 95:14470-14475 (1998).
77. not used

What is claimed is:

1. A method of decreasing viral replication of a human cytomegalovirus in cells, the method comprising decreasing levels of functional cellular protease in the cells by exposing the cells to a calpain inhibitor, wherein the cells are infected with the human cytomegalovirus and wherein the calpain inhibitor is E64d or Z-Leu-Leu-H, wherein the calpain inhibitor increases the levels of p21$^{cip1}$ in the cells whereby viral replication of a human cytomegalovirus is decreased.

2. The method of claim 1 wherein the cellular protease is calpain.

3. A method of treating a viral infection of a human cytomegalovirus in a subject, the method comprising administering to the subject an amount of a compound effective to decrease levels of functional cellular protease in cells of the subject wherein the compound increases the levels of p21$^{cip1}$ in the cells whereby viral replication of a human cytomegalovirus is decreased and the compound is E64d or Z-Leu-Leu-H.

4. The method of claim 3 wherein the cellular protease is calpain.

* * * * *